United States Patent [19]

Peak

[11] 4,123,936
[45] Nov. 7, 1978

[54] VOLUMETER DEVICE

[75] Inventor: William H. Peak, Albany, N.Y.

[73] Assignee: Donald P. Matula, Schenectady, N.Y.; a part interest

[21] Appl. No.: 770,206

[22] Filed: Feb. 18, 1977

Related U.S. Application Data

[63] Continuation of Ser. No. 667,491, Mar. 17, 1976, abandoned, which is a continuation-in-part of Ser. No. 460,567, Apr. 12, 1974, abandoned.

[51] Int. Cl.² ............................................. G01F 17/00
[52] U.S. Cl. ....................................... 73/149; 73/433
[58] Field of Search ................... 33/1 V; 73/149, 427, 73/433; 215/7, DIG. 8; 222/29

[56] References Cited

U.S. PATENT DOCUMENTS

| 524,766 | 8/1894 | Ogram | 73/427 |
| 2,353,792 | 7/1944 | Sowell | 73/149 |

OTHER PUBLICATIONS

"Public Roads", vol. 22, No. 12, Feb. 1942, pp. 279–280, Publication of U.S. Federal Bureau of Public Roads.

Primary Examiner—James J. Gill
Attorney, Agent, or Firm—Gerhard K. Adam

[57] ABSTRACT

A volumeter apparatus for use in soil density determinations is described whereby direct and reproducible readings may be made visually by means of a scale on the apparatus which is based upon the inversion of a sand charge remaining in the apparatus.

7 Claims, 1 Drawing Figure

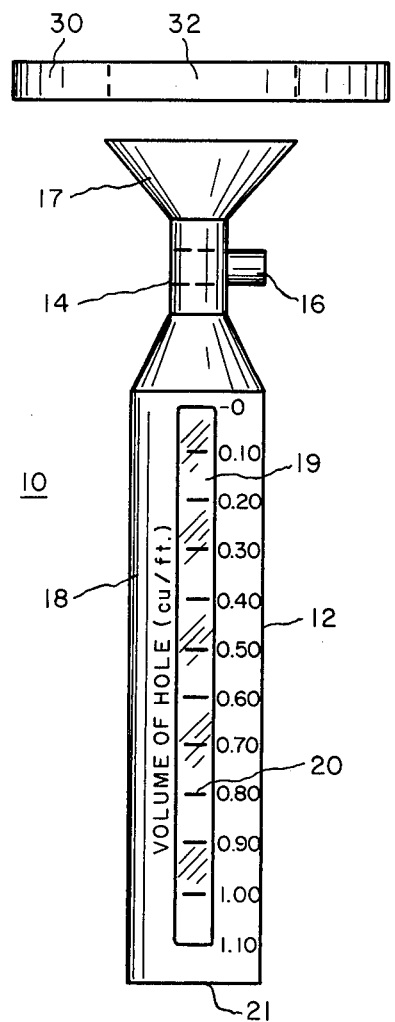

VOLUMETER DEVICE

This application is a continuation of application Ser. No. 667,491, filed Mar. 17, 1976, now abandoned, which in turn was a continuation-in-part of application Ser. No. 460,567, filed Apr. 12, 1974, now abandoned.

The present invention relates to a volumeter.

Prior art devices for determining soil density suffer from the drawback of requiring, for measuring the volume of an excavation, the use of an inflatable or otherwise fillable bladder or requiring the weighing of the apparatus used to provide material for filling an excavation. The present invention overcomes these disadvantages and provides benefits of direct reading of the volume of the excavation as well as others.

BRIEF DESCRIPTION OF DRAWING

FIG. 1 is a front elevation view of the volumeter of the present invention, shown with a plate with which the volumeter can be used.

PREFERRED EMBODIMENT

In the invention, the volumeter 10 comprises a main body portion 12 having a neck portion 14 comprising an open end, a valve member 16 at the neck portion, and a mouth portion 17 connected to the opening of the neck portion 14. The body portion 12 includes a wall 18 comprising at least a part 19 that is transparent or translucent, the wall 18 bearing a graduated scale 20, at the transparent or translucent wall part 19. It is preferred that the volumeter 10 comprise a plurality, e.g., three of identical such graduated scales 20 distributed around the perimeter of the main body portion 12 and that such scales 20 be, more or less, evenly spaced thereabout and substantially equidistant from each other and from the ends of the main body portion 12. Such a plurality of scales 20 facilitates leveling the sand or other material contained by the main body portion 12 and used for determining soil density. The body portion 12 comprises an open end at which the valve member 16 is disposed, the other end 21 of the body portion 12 being closed.

A soil density measuring device of the type disclosed in "Public Roads", February 1942, at pages 279 et seq., can be read after the test hole is filled, without further manipulation of the device, but this leads to problems of reproducability and accuracy of the readings, as explained below. Further, such device, as stated in the article, requires that the volumetric readings be made carefully and care be exercised not to compact the sand during the operation.

The body portion 12 preferably has a cylindrical configuration, although other shapes can be used satisfactorily. It is preferred that the entire body portion 12 be transparent although a body portion having a wall part or an entire wall that is translucent can be used with satisfactory results. The body portion 12 can be of glass or plastic, for example.

The graduated scale 19, which can measure the volume of the contents of the body portion interior, is disposed such that the lower end of the scale, for example, is located closer to the valve member 16, the scale ascending in value in the direction away from the valve member. While the scale depicted in the FIGURE is shown to have specific values and units, the scale and/or units can be changed or varied therefrom.

The mouth portion 17 preferably is substantially funnel shaped, e.g., a frusto-conical shape, the narrower end of the mouth portion being connected to the neck portion 14.

Using the volumeter apparatus 10 according to one mode of operation for testing soil density by "in-place" techniques, the user first fills the volumeter body portion 12 with sand, for example, the sand being introduced into the interior space of the body portion 12 through the mouth portion 17 and valve member 16. While the sand is being filled into it, the apparatus 10 is, for more accurate results, placed on a firm level surface, the funnel shaped mouth portion 17 preferably being kept at least half full all the time the sand is being thus introduced. When the flow of sand into the body portion ceases, the valve member 16 is carefully closed to avoid disturbing the volume of sand in the body portion and the sand remaining in the mouth portion 17 is removed. By charging the apparatus 10 in the same manner from test to test, a generally constant sand density is obtained for the sand charge immediately following such charging step. However, due to the movement of other manipulation, handling, or transportation of the charged apparatus, including the positioning of the apparatus for filling the hole the density of the sand charge remaining in the apparatus after a partical discharge of the sand to fill the hole, is variable because of compaction effects so that any reading of the volume of such remaining sand immediately following such discharge without any further manipulation of the apparatus containing the remaining sand, will result in an inaccurate such reading. It is necessary that such remaining sand have, in each test, at the time of reading, a constant, reproducible density from test to test in order to eliminate the inaccuracy introduced into the final reading by the above variation in the density of such sand remaining in the unmanipulated apparatus. The present invention overcame or at least substantially alleviates this problem as described below.

To prepare a hole in the ground for making the soil density test, a base plate 30 having a central aperture 32, and preferably having an annular ring configuration, is firmly placed on a level area of the ground and a hole having a diameter substantially equal to the plate aperture is dug through the plate aperture to a depth of, for example, about 4 inches or more and preferably about 6 inches or more below the bottom of the plate.

To determine the volume of this hole, the mouth portion 17 of the apparatus 10 is inverted and located on the base plate 30 with the wider end of the mouth portion placed over and aligned with the central aperture 32 of base plate. The valve member 16 is opened, permitting the sand to flow into the hole, the valve member 16 being closed when the hole is filled the apparatus 10 being in a mouth portion-down position. The apparatus 10 is again inverted and then righted to its position with the mouth portion 17 up, the apparatus 10 then being gently shaken in a horizontal (i.e., side-to-side) direction to level the said contained by the body portion. The volume of the sand transferred to the hole is then read directly from the scale by locating the top of the sand column in the body portion, via the translucent or transparent area 19 of the body portion wall and measuring the level of the same column top on the graduated scale 20. The volume of the sand transferred to the hole provides the volume of the excavated hole. The graduated scale is permanently adjusted to compensate for sand that fills the mouth portion and the base plate aperture when the excavated hole is filled, thus providing a direct measure of the hole volume only. Therefore, in order that a reproducible reading of the test density and, therefore, more accurate and reproducible measurements be obtained, there is carried out the above-described step of righting the apparatus (i.e., placing the apparatus in a mouth portion-up position) charged with the sand after the test hole is filled with the sand from the apparatus. This righting step renders the remaining sand of the apparatus, in a substantially reproducible and substantially constant level sand density (hereinafter referred to as the "sand reading density"). It is important that the scales 20 of the apparatus 10 are adjusted for the sand reading density which is generally the same or at least substantially equal for a wide variety of sands so as to provide a measurement of the volume of the sand remaining in the apparatus and at this substantially constant density, i.e., sand reading density, or density at the time of measurement of the remaining sand volume. It is of further importance that the scale can be, and preferably is, compensated for the alteration of the sand density resulting from the side-to-side movement of the apparatus that is done to achieve a more level top surface of the same column. It is important that the scale 20 ascend in value in the direction away from the valve member 16 and mouth portion 17, so as to allow the reading to be made of the remaining sand volume without the need for any further manipulation of the apparatus to achieve a sand density reading position. By locating such scale 20 so as to ascend in value in the direction away from such valve member 16 and mouth portion 17, the user of the apparatus is compelled to invert the apparatus after a portion of the sand charge is transferred to the hole, so that, consequently, it is not possible to obtain a final volume reading of the sand remaining in the apparatus without first going through this apparatus inversion step that provides a reliable and reproducible sand reading density.

The soil removed in making the hole is weighed and the soil density of the examined ground area is determined by dividing the soil weight by the volume of the hole as the latter is measured in the above-described manner. In addition to the foregoing advantages, the present invention permits soil density measurements to be made without substantial variation in test results arising from weight changes in the sand brought about by moisture absorption thereby, specific gravity variations, etc.

According to the invention, the funnel or mouth portion 17 is permanently secured to the body portion 12 to provide a unitary structure from which the mouth portion is not removable. As a result of this, the volumeter 10 is required to be charged with sand that is passed through the valve member, leading to more reproducible results insofar as the initial charge density (or filling density), than in the case where the funnel is removable and the sand charge is introduced through the open end of the body portion 12. The passage of the sand through the valve member serves to regulate the sand flow into the body portion and allows the sand to follow a more-or-less constant path when entering the body portion 12.

I claim:
1. A volumeter apparatus, comprising
   (a) a hollow main body portion comprising an open end, a second end which is closed and at least a wall portion that is one of substantially transparent and substantially translucent, said wall portion comprising at least one scale adapted to provide a direct reading of the volume of the cavity to be measured;
   (b) a mouth portion disposed at said open end;
   (c) a valve means disposed between said main body portion and said mouth portion for controlling material flow therebetween; and
   (d) said one scale having values decreasing in magnitude in the direction toward said mouth portion.
2. A volumeter apparatus as defined in claim 1, wherein said body portion is of substantially cylindrical configuration.
3. A volumeter apparatus as defined in claim 1, wherein the wall of said body portion is one of completely transparent and translucent.
4. A volumeter apparatus as defined in claim 3, wherein said body portion is one of glass and plastic.
5. A volumeter apparatus as defined in claim 1, wherein said main body portion comprises a neck portion, said valve means being located at said neck portion.
6. A volumeter apparatus as defined in claim 1, comprising a plurality of said scales.
7. A volumeter apparatus as defined in claim 6, wherein said scales are substantially equidistant from each other and substantially co-extensive.

* * * * *